(12) United States Patent
Chang et al.

(10) Patent No.: US 11,478,498 B2
(45) Date of Patent: *Oct. 25, 2022

(54) TOPICAL PHARMACEUTICAL FORMULATIONS CONTAINING A LOW CONCENTRATION OF BENZOYL PEROXIDE IN SUSPENSION IN WATER AND A WATER-MISCIBLE ORGANIC SOLVENT

(71) Applicant: Dow Pharmaceutical Sciences, Inc., Petaluma, CA (US)

(72) Inventors: Yunik Chang, Clermont, FL (US); Gordon J. Dow, Greenbrae, CA (US); Radhakrishnan Pillai, Santa Rosa, CA (US)

(73) Assignee: Dow Pharmaceutical Sciences, Inc., Petaluma, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/853,361

(22) Filed: Apr. 20, 2020

(65) Prior Publication Data

US 2020/0276218 A1    Sep. 3, 2020

Related U.S. Application Data

(60) Continuation of application No. 16/171,862, filed on Oct. 26, 2018, now Pat. No. 10,624,918, which is a continuation of application No. 15/332,933, filed on Oct. 24, 2016, now Pat. No. 10,137,142, which is a continuation of application No. 14/260,211, filed on (Continued)

(51) Int. Cl.
| | |
|---|---|
| *A61K 31/7056* | (2006.01) |
| *A61K 31/075* | (2006.01) |
| *A61K 47/10* | (2017.01) |
| *A61K 8/02* | (2006.01) |
| *A61K 8/04* | (2006.01) |
| *A61K 8/34* | (2006.01) |
| *A61K 8/55* | (2006.01) |
| *A61Q 19/00* | (2006.01) |
| *A61K 9/00* | (2006.01) |
| *A61K 31/327* | (2006.01) |
| *A61K 31/235* | (2006.01) |
| *A61K 8/38* | (2006.01) |
| *A61K 45/06* | (2006.01) |

(Continued)

(52) U.S. Cl.
CPC ........ *A61K 31/7056* (2013.01); *A61K 8/0241* (2013.01); *A61K 8/042* (2013.01); *A61K 8/044* (2013.01); *A61K 8/345* (2013.01); *A61K 8/38* (2013.01); *A61K 8/55* (2013.01); *A61K 9/0014* (2013.01); *A61K 9/14* (2013.01); *A61K 31/075* (2013.01); *A61K 31/235* (2013.01); *A61K 31/327* (2013.01); *A61K 45/06* (2013.01); *A61K 47/10* (2013.01); *A61K 47/32* (2013.01); *A61Q 19/00* (2013.01); *A61K 2800/33* (2013.01); *A61K 2800/413* (2013.01)

(58) Field of Classification Search
CPC .. A61K 31/7056; A61K 8/0241; A61K 8/042; A61K 8/044; A61K 8/345; A61K 8/38; A61K 8/55; A61K 9/014; A61K 9/14; A61K 31/075; A61K 31/235; A61K 31/327; A61K 45/06; A61K 47/10; A61K 47/32; A61K 2800/33; A61K 2800/413; A61Q 19/00

See application file for complete search history.

(56) References Cited

U.S. PATENT DOCUMENTS

| | | |
|---|---|---|
| 3,535,442 A | 10/1970 | Cox et al. |
| 4,056,611 A | 11/1977 | Young |

(Continued)

FOREIGN PATENT DOCUMENTS

| | | |
|---|---|---|
| GB | 1 594 314 | 7/1981 |
| JP | H07-504168 A | 5/1995 |

(Continued)

OTHER PUBLICATIONS

Andres, P. et al., "Adapalene-Benzoyl Peroxide once-daily, fixed-dose combination gel for the treatment of acne vulgaris: A randomized, bilateral (split-face), dose-assessment study of cutaneous tolerability in healthy participants," Cutis, 81:278-284 (2008).

(Continued)

*Primary Examiner* — James D. Anderson
*Assistant Examiner* — William Y Lee
(74) *Attorney, Agent, or Firm* — Kilpatrick Townsend & Stockton LLP

(57) ABSTRACT

An aqueous formulation for topical application to the skin comprising water, a water-miscible organic solvent, and benzoyl peroxide, wherein the concentration of the organic solvent is sufficient to provide a stable suspension of benzoyl peroxide in the aqueous formulation without the inclusion of a surfactant in the formulation, wherein the ratio of concentrations of water and organic solvent in the formulation is sufficient to maintain the benzoyl peroxide in saturated solubility in the formulation following application to the skin, and wherein the concentration of benzoyl peroxide in the formulation is less than 5.0% and at least 1.0% w/w. The formulation may further contain a chemical compound in addition to benzoyl peroxide that is effective in the treatment of acne. The aqueous formulations of the invention are useful in the treatment of acne and acne rosacea.

8 Claims, No Drawings

Related U.S. Application Data

Apr. 23, 2014, now Pat. No. 9,504,704, which is a continuation-in-part of application No. 13/613,401, filed on Sep. 13, 2012, now Pat. No. 9,693,988, which is a division of application No. 12/455,525, filed on Jun. 3, 2009, now Pat. No. 8,288,434.

(60) Provisional application No. 61/131,014, filed on Jun. 5, 2008.

(51) Int. Cl.
*A61K 9/14* (2006.01)
*A61K 47/32* (2006.01)

(56) References Cited

U.S. PATENT DOCUMENTS

| | | | |
|---|---|---|---|
| 4,075,353 | A | 2/1978 | Mandy et al. |
| 4,189,501 | A | 2/1980 | Fulton |
| 4,387,107 | A | 6/1983 | Klein et al. |
| 4,401,835 | A | 8/1983 | Tarasov |
| 4,411,893 | A | 10/1983 | Johnson et al. |
| 4,497,794 | A | 2/1985 | Klein et al. |
| 4,803,228 | A | 2/1989 | Jacquet et al. |
| 4,923,900 | A | 5/1990 | De Villez |
| 5,445,823 | A | 8/1995 | Hall et al. |
| 5,446,028 | A | 8/1995 | Klein |
| 5,466,446 | A | 11/1995 | Stiefel |
| 5,733,886 | A | 3/1998 | Baroody |
| 5,767,098 | A | 6/1998 | Klein |
| 6,117,843 | A | 9/2000 | Baroody |
| 6,387,383 | B1 | 5/2002 | Dow et al. |
| 6,433,024 | B1 | 8/2002 | Popp et al. |
| 7,153,888 | B2 | 12/2006 | Schwarz |
| 8,288,434 | B2 | 10/2012 | Chang et al. |
| 8,663,699 | B2 | 3/2014 | Chang et al. |
| 8,895,070 | B2 | 11/2014 | Chang et al. |
| 9,078,870 | B2 | 7/2015 | Chang |
| 9,504,704 | B2 | 11/2016 | Chang |
| 9,561,208 | B2 | 2/2017 | Chang |
| 9,693,988 | B2 | 7/2017 | Chang |
| 10,137,142 | B2 * | 11/2018 | Chang .............. A61K 9/0014 |
| 10,220,049 | B2 * | 3/2019 | Chang .............. A61Q 19/00 |
| 10,624,918 | B2 * | 4/2020 | Chang .............. A61K 45/06 |
| 2002/0039561 | A1 | 4/2002 | Doughty et al. |
| 2003/0064084 | A1 | 4/2003 | Bhagwat et al. |
| 2003/0170196 | A1 | 9/2003 | Orsoni et al. |
| 2004/0101566 | A1 | 5/2004 | Cooper et al. |
| 2005/0239723 | A1 | 10/2005 | Amin et al. |
| 2006/0204530 | A1 | 9/2006 | Ramirez |
| 2007/0003585 | A1 | 1/2007 | Clark et al. |
| 2007/0077208 | A1 | 4/2007 | Abram et al. |
| 2007/0237724 | A1 | 10/2007 | Abram et al. |
| 2010/0166852 | A1 | 7/2010 | Mallard et al. |
| 2013/0012460 | A1 | 1/2013 | Chang et al. |
| 2013/0171283 | A1 | 7/2013 | Florence |
| 2013/0236549 | A1 | 9/2013 | Chang et al. |
| 2014/0050792 | A1 | 2/2014 | Chang et al. |
| 2014/0051649 | A1 | 2/2014 | Chang et al. |
| 2014/0134252 | A1 | 5/2014 | Chang et al. |
| 2020/0297684 | A1 * | 9/2020 | Pillai .............. A61P 17/10 |

FOREIGN PATENT DOCUMENTS

| | | |
|---|---|---|
| JP | 2005-513146 A | 5/2005 |
| JP | 2010-513428 A | 4/2010 |
| WO | 81/00206 A1 | 2/1981 |
| WO | 93/15726 A1 | 8/1993 |
| WO | 93/20796 A1 | 10/1993 |
| WO | 95/31978 A1 | 11/1995 |
| WO | 2007/002831 A2 | 1/2007 |
| WO | 2008/017914 | 2/2008 |
| WO | 2008/107193 A1 | 9/2008 |

OTHER PUBLICATIONS

Benzac AC® 2 1/2 Gel Product.
Benzac AC® Wash 2 1/2 Product.
Benzac W®, Physicians' Desk Reference, Medical Economics Co., 43rd ed. 1989, p. 1518.
Benzac W® 2 1/2 Gel Water Base Gel Product.
BenzaClin™ Topical Gel, Physicians' Desk Reference, Medical Economics Co., 56th ed. 2002, pp. 1220-1221.
Benzamycin® Gel Product.
Billany , M., "Dosage form design and manufacture," Ch. 23, pp. 334-359, in Pharmaceutics: The Science of Dosage Form Design (2nd ed. 2002).
Chellquist, E.M. et al., "Benzoyl peroxide solubility and stability in hydric solvents," Pharm Res, vol. 9, pp. 1341-1346 (1992).
Cleocin T® Topical Gel.
Cleocin T® Topical Solution.
Clinac BPO 7 Gel Product.
Clindagel® Topical Gel, Feb. 2007 (date determined by Examiner in U.S. Appl. No. 13/869,494).
Clindets® Pledgets.
Complaint filed in the US District Court for the District of New Jersey (*Dow Pharmaceutical Sciences Inc. et al.* vs. *Actavis, Inc. et al.*) (filed Oct. 24, 2013).
Complaint filed in the US District Court for the District of New Jersey (*Dow Pharmaceutical Sciences Inc. et al.* vs. *Perrigo Company*) (filed Nov. 15, 2013).
Dermik Laboratories, "Benzaclin Topical Gel Prescribing Information" (2007).
DESQUAM-E™ 2.5 Emollient Gel Product.
DESQUAM-X® 2.5 Gel Product.
Dow, Gordon J., "Declaration of Gordon Dow under 37 C.F.R. § 1.132 in U.S. Appl. No. 13/869,494," Nov. 12, 2013, 10 pages.
DUAC® Gel Product.
First Office Action mailed in connection with corresponding Japanese Application No. 2011-512469; 2 PP.
International Search Report issued in connection with corresponding International Application No. PCT/US09/03367, dated Jul. 16, 2009, 1 page.
Kligman, A.M. et al., "New uses for benzoyl peroxide: a broad-spectrum antimicrobial agent," Int J Dermatology, vol. 16, pp. 413-417 (1977).
Kligman, A.M., "Acne vulgaris: tricks and treatments, Part II: the benzoyl peroxide saga," Cutis: Cutaneous Medicine for the Practitioner, vol. 56, pp. 260-261 (1995).
Labeling for Benzaclin™ Topical Gel Product, Dec. 21, 2000.
Labeling for Benzamycin® Gel Product, Jan. 27, 2003.
Labeling for Cleocin T® Topical solution and Topical Gel Products, Jul. 14, 2002.
Labeling for Clindagel® Topical Gel, Nov. 27, 2000.
Labeling for DUAC® Gel Product, Aug. 26, 2002.
Lassus, A., "Local treatment of acne. A clinical study and evaluation of the effect of different concentrations of benzoyl peroxide gel," Curr Med Res Opin, 7(6): 370-373 (1981).
Leyden, James J. and Alan R. Shalita, "Rational therapy for acne vulgaris: An update on topical treatment," Journal of the American Academy of Dermatology, vol. 15, No. 4, Part 2, Oct. 1986, pp. 907-915.
Leyden, James J. et al., "Topical antibiotics and topical antimicrobial agent in acne therapy," Acta Dermatovener (Stockholm), Suppl. 89, 1980, pp. 75-82.
Leyden, James J., "Therapy for acne vulgaris," The New England Journal of Medicine, Apr. 17, 1997, pp. 1156-1162.
Mills, Oh et al., "Comparing 2.5%, 5%, and 10% benzoyl peroxide on inflammatory acne vulgaris," Int J Dermatology, vol. 25(10), pp. 664-667 (1986).
Nguyen, Q.H. et al., "Management of acne vulgaris," American Family Physician, vol. 50, pp. 89-96 (1994).
Panoxyl AQ 2 1/2, Physicians' Desk Reference, Medical Economics Company, Inc. 43rd ed. 1989, 2115.
Panoxyl® AQ 2Yz Product.
Physicians' Desk Reference (Medical Economics Co., 46th ed. 1992) (pp. 907-908, 1681-1682, 2264, 2327-2328, and 2397-2398).

(56) References Cited

OTHER PUBLICATIONS

Physicians' Desk Reference (Medical Economics Co., 53rd ed. 1999) (pp. 910-911, 1048-1049, 2464-2465, 3132-3133, 3242-3243).
Physicians' Desk Reference (Thomson PDR, 60th ed. 2006) (pp. 1046-1048, 1137, 1207, 1864, and 3212-3215).
Physicians' Desk Reference for Nonprescription Drugs (1980) (pp. 416, 422, 527-528, 553, 628-629, 640, and 646).
Physicians' Desk Reference for Nonprescription Drugs (1981) (pp. 416, 424, 528, 543, 555, 587, 592, 637-638, 648, and 656).
Physicians' Desk Reference for Nonprescription Drugs (1982) (pp. 417, 427, 539, 558, 604-605, 655-656, 667, and 675).
Physicians' Desk Reference for Nonprescription Drugs (1983) (pp. 415-416, 426-427, 514, 548, 614-615, and 687-688).
Physicians' Desk Reference for Nonprescription Drugs (1984) (pp. 412, 416-417, 428-429, 542, 572, 620 694-695, and 716).
Physicians' Desk Reference for Nonprescription Drugs (1985) (pp. 413, 418, 423, 433, 542, 574, 623, 651-652, 712-712, and 725).
Physicians' Desk Reference for Nonprescription Drugs (1986) (pp. 417, 423, 432, 547, 631, 661-662, 715-716, and 732).
Physicians' Desk Reference for Nonprescription Drugs (1987) (pp. 415-416, 422, 550, 559, 624-626, 640, 663, and 738-739).
Physicians' Desk Reference for Nonprescription Drugs (1988) (pp. 415, 421, 432, 541 ,617, 619, 634, 655-656, and 726-727).
Physicians' Desk Reference for Nonprescription Drugs (1989) (pp. 416-417, 422, 429, 434, 544-545, 619-622, 653-654, 695, and 728-729).
Physicians' Desk Reference for Nonprescription Drugs (1990) (pp. 418, 424, 430-431, 618-619, 646, 699-701, and 706).
Physicians' Desk Reference for Nonprescription Drugs (1991) (pp. 425, 431-433, 658, 709, and 719-721).
Physicians' Desk Reference for Nonprescription Drugs (1992) (pp. 426-427, 704, and 715-716).
Physicians' Desk Reference for Nonprescription Drugs (1993) (pp. 426, 428, 643, 715, 729-730).
Physicians' Desk Reference for Nonprescription Drugs (1994) (pp. 425-426, 630-631, 702, and 717).
Physicians' Desk Reference for Nonprescription Drugs (1995) (p. 749).
Physicians' Desk Reference for Nonprescription Drugs (1996) (p. 722).
Pray, W.S., Nonprescription Product Therapeutics, pp. 530-540 (1996).
Relyveld et al., "Benzoyl peroxide/clindamycin/UVA is more effective than fluticasone/UVA in progressive macular hypomelanosis: A randomized study," Journal of the American Academy of Dermatology, vol. 55, Issue 5, Nov. 2006, pp. 836-843.
Statement concerning alleged prior art products, Dec. 23, 2013.
Statement concerning related, unpublished, co-pending applications.
Supplementary European Search Report mailed in connection with corresponding European Application No. 09758748, dated Oct. 4, 2013, 1 page.
Topical Acne Drug Products for Over-the-Counter Human Use; Tentative Final Monograph; HHS Notice of Proposed Rulemaking; 50 Fed. Reg. 2172 (Jan. 15, 1985) (to be codified at 21 CFR Part 333).
Triaz®, Physicians' Desk Reference, Thomson PDR, 61st ed. 2007, pp. 1892-1893.
TRIAZ® 3% Gel Product.
UNEP (United Nations Environment Programme) Publications, Benzoyl Peroxide: CAS No. 94-36-0 (2002).
Yong, Chuah Chong, "Benzoyl peroxide gel therapy in acne in Singapore," International Journal of Dermatology, Jul.-Aug. 1970, vol. 18, pp. 485-488.
U.S. Appl. No. 13/869,494 (now U.S. Pat. No. 8,663,699).
U.S. Appl. No. 14/065,186 (now U.S. Pat. No. 8,895,070).
U.S. Appl. No. 14/065,199 (now U.S. Pat. No. 9,078,870).
U.S. Appl. No. 14/065,207 (now abandoned).
U.S. Appl. No. 15/094,895 (now U.S. Pat. No. 9,561,208).
U.S. Appl. No. 15/425,844 (now U.S. Pat. No. 10,220,049).

* cited by examiner

TOPICAL PHARMACEUTICAL FORMULATIONS CONTAINING A LOW CONCENTRATION OF BENZOYL PEROXIDE IN SUSPENSION IN WATER AND A WATER-MISCIBLE ORGANIC SOLVENT

CROSS-REFERENCES TO RELATED APPLICATIONS

This application is a continuation of U.S. application Ser. No. 16/171,862, filed Oct. 26, 2018; which is a continuation of U.S. application Ser. No. 15/332,933, filed Oct. 24, 2016; which is a continuation of U.S. application Ser. No. 14/260,211, filed Apr. 23, 2014; which is a continuation-in-part of U.S. application Ser. No. 13/613,401, filed Sep. 13, 2012; which is a division of U.S. application Ser. No. 12/455,525, filed Jun. 3, 2009; which claims priority from U.S. Provisional Patent Application Ser. No. 61/131,014, filed Jun. 5, 2008; which applications are incorporated herein by reference in their entirety.

FIELD OF THE INVENTION

The present invention pertains to the field of topically applied pharmaceutical formulations for the treatment of dermatologic conditions. In particular, the invention pertains to formulations containing benzoyl peroxide and optionally an anti-acne compound such as an antibiotic.

BACKGROUND OF THE INVENTION

Benzoyl peroxide is commonly used in topical pharmaceutical formulations to treat dermatologic conditions such as acne vulgaris, commonly referred to as acne. Topically applied antibiotics have also been used in topical formulations to treat dermatologic conditions such as acne. Examples of antibiotics that have been used topically to treat acne include macrolide antibiotic such as erythromycin and lincomycin-type antibiotics such as clindamycin and lincomycin.

Combination products containing benzoyl peroxide and an antibiotic have been utilized and provide increased anti-acne efficacy compared to formulations containing either benzoyl peroxide or an antibiotic alone. Klein, U.S. Pat. No. 4,497,794, discloses a combination formulation containing benzoyl peroxide and erythromycin for the treatment of acne. Compositions prepared generally as described in Klein '794 are marketed under the tradename Benzamycin® (Dermik Laboratories, Berwyn, Pa.). Combinations of benzoyl peroxide and lincomycin family antibiotics such as clindamycin are disclosed in Klein, U.S. Pat. No. 5,767,098, Baroody, U.S. Pat. No. 5,733,886, and Stiefel, U.S. Pat. No. 5,466,446. Compositions prepared generally as described in Klein '098 are marketed under the tradename Benzaclin® (Dermik Laboratories) and as described in Stiefel are marketed under the tradename Duac® (Stiefel Laboratories, Inc., Coral Gables, Fla.).

One of the problems associated with topical therapy with compositions containing benzoyl peroxide, either alone or in combination with an antibiotic, is the localized irritation at the site of application. Benzoyl peroxide has been shown to have a concentration dependent irritation potential. See Mills et al, International Journal of Dermatology, 25(10): 664-667 (1986) and Lassus, Current Medical Research and Opinion, 7(6):370-373 (1981). Each of the above products contains benzoyl peroxide at a concentration of 5% w/w, a concentration that is associated with irritation.

Benzoyl peroxide is practically insoluble in water. The irritation due to application of compositions containing benzoyl peroxide has been determined to be caused by the portion of the benzoyl peroxide that is in suspension, whereas dissolved benzoyl peroxide causes little or no skin irritation. See, Schwarz, U.S. Pat. No. 7,153,888; and De Villez, U.S. Pat. No. 4,923,900. Schwarz discloses a composition containing benzoyl peroxide wherein all of the benzoyl peroxide of the composition is in solution in an organic solvent. Because dissolution of benzoyl peroxide accelerates the degradation of benzoyl peroxide, Schwarz discloses that an antioxidant is included in the composition to improve the stability of the solution.

One disadvantage of Schwarz is that a high concentration of organic solvent is required in order to dissolve the benzoyl peroxide. High concentrations of organic solvents have a tendency to be irritating to skin, primarily due to the drying effect due to solubilization of skin lipids. In Tables 1 to 3, Schwarz discloses multiple examples of compositions containing various organic solvents and benzoyl peroxide. In each of the examples, the concentration of organic solvent is more than 10 times, and generally more than 15 times that of the benzoyl peroxide in the composition.

De Villez discloses a composition containing benzoyl peroxide, water, and a water-miscible organic solvent that is less volatile than water and in which the benzoyl peroxide is soluble. Prior to application on the skin, the benzoyl peroxide is in suspension in the composition. However, when applied to the skin, the water from the composition evaporates relatively rapidly compared to the organic solvent. The benzoyl peroxide of the composition is then dissolved in situ in the organic solvent, resulting in a solution of benzoyl peroxide after all of the water has evaporated.

In order for the De Villez composition to be transformed from a suspension to a solution, the composition must remain in residence on the skin surface for a sufficient time for the water in the composition to evaporate. During this time, the benzoyl peroxide is in suspension in the composition and the suspended particles are able to interact with the skin to cause irritation. Moreover, De Villez, like Schwarz, requires a relatively high concentration of an organic solvent, which may contribute to the irritation potential of such compositions.

DESCRIPTION OF THE INVENTION

It has been surprisingly discovered that substantially similar clinical anti-acne efficacy obtained by use of an aqueous topical formulation containing 5.0% benzoyl peroxide is obtained by providing an aqueous topical formulation containing a suspension of a low concentration of benzoyl peroxide in a saturated solution of water and a water-miscible organic solvent. All % concentrations in this specification refer to % w/w. The formulation of the invention reduces skin irritation due to application of the formulation compared to application of a similar 5.0% benzoyl peroxide formulation without compromising clinical efficacy.

In one embodiment, the invention is a pharmaceutical formulation for topical application containing water, a water-miscible organic solvent, wherein the ratio of concentrations of the water and the organic solvent is high, and benzoyl peroxide, wherein the concentration of benzoyl peroxide in the formulation is low. As used herein, the term "low concentration", when referring to the concentration of benzoyl peroxide in a formulation, means less than 5.0% w/w. Preferably, the pharmaceutical formulation is an aqueous gel formulation. Preferably, the pharmaceutical formulation is free of surfactants.

The benzoyl peroxide is distributed in the formulation as a uniform suspension. Preferably, the suspended benzoyl peroxide has a mean particle size of less than 100 microns, more preferably between 1 and 50 microns, and most preferably between 2.5 and 30 microns Necessarily, a portion of the benzoyl peroxide will also be dissolved in the organic solvent and a small portion of the benzoyl peroxide will be dissolved in the water. Accordingly, the formulation is a saturated solution of benzoyl peroxide with a dissolved concentration of benzoyl peroxide that is higher than when dissolved in water without the organic solvent.

In a preferred embodiment, but not necessarily, the formulation of the invention contains at least one additional chemical compound that is effective in the treatment of acne. The anti-acne compound may be suspended or dissolved in the formulation. Preferably, the anti-acne compound is soluble in water and so is dissolved in the formulation. One such preferred anti-acne compound is an antibiotic. Preferred antibiotics include those of the macrolide family of antibiotics such as erythromycin, azithromycin, clarithromycin, tilmicosin, and tylosin, and those of the lincomycin family of antibiotics such as clindamycin and lincomycin. A particularly preferred antibiotic to be used in combination with benzoyl peroxide in the formulation of the invention is clindamycin, such as clindamycin hydrochloride or clindamycin phosphate. Additional topical anti-acne active ingredients that may be contained in the formulation of the invention, either with or without the inclusion of an antibiotic, include salicylic acid, azelaic acid, niacinamide, urea, and retinoids such as tretinoin, adapalene and tazarotene.

The additional anti-acne compound, if present in the formulation of the invention, is preferably present in a concentration in which there is a demonstrable anti-acne effect in the absence of benzoyl peroxide. For example, if clindamycin is present in the formulation of the invention, the concentration of the clindamycin is preferred to be at least 0.5% with a preferred concentration of 1%. Higher concentrations of clindamycin, such as 2.5% or 5.0% or higher may be utilized in the formulation.

The organic solvent of the formulation of the invention has the following characteristics:
(1) is miscible in water,
(2) does not chemically react with benzoyl peroxide at temperatures between 0° C. and 40° C.,
(3) is a liquid at temperatures between 0° C. and 40° C.,
(4) is capable of dissolving benzoyl peroxide at a concentration of at least 0.1% at an ambient temperature,
(5) is capable of dispersing benzoyl peroxide in an aqueous gel in the absence of a surfactant.

An example of a preferred organic solvent for the formulation of the invention is a polyol, also known as a polyhydric alcohol. Representative examples of polyols include glycols and sugar alcohols. Preferred polyols for the formulation of the invention include polyether glycols, such as ethoxydiglycol, and propylene glycol. A preferred water-miscible organic solvent is propylene glycol. The inventors have determined by HPLC analysis that benzoyl peroxide is soluble in 100% propylene glycol at room temperature at a level between 0.2% and 0.3% w/w. A second preferred organic solvent is ethoxydiglycol, such as sold under the tradename Transcutol® (Gattefosse, Saint-Priest, France). It has been determined by HPLC analysis that benzoyl peroxide is soluble in ethoxydiglycol at room temperature at a level of about 4.9%. Another preferred organic solvent is polyethylene glycol, such as PEG 400.

The concentration of the organic solvent in the formulation should be sufficiently high to provide a stable suspension of benzoyl peroxide in an aqueous fluid without the presence of a surfactant. The concentration of the organic solvent should be lower than that which will dissolve all of the benzoyl peroxide in the formulation following the removal of all of the water from the formulation. Generally, the concentration of the organic solvent should be between one and four times the concentration of benzoyl peroxide in the formulation.

Additionally, the ratio of concentrations of water and organic solvent in the formulation should be high, so as to maintain the benzoyl peroxide at or near saturated solubility in the residual formulation, that remaining on the skin after application of the formulation with subsequent evaporation of water from the formulation, thereby maximizing the thermodynamic activity of the benzoyl peroxide in the residual formulation on the skin. It is therefore preferred that, in the formulation of the invention, the relative concentrations of water and the organic solvent should be at least 7:1, such as at least 9:1 or 10:1, preferably at least 12:1, and most preferably at least 20:1, such as up to 98:1.

The concentration of benzoyl peroxide in the formulation is an amount that is less than 5.0% and that is effective to treat the signs and/or symptoms of acne. At the concentrations of benzoyl peroxide in the formulation of the invention, skin irritation is reduced compared to formulations containing 5.0% benzoyl peroxide. Therefore, concentrations of benzoyl peroxide between 1.0% and 4.5% are suitable for invention. A preferred range of benzoyl peroxide concentrations is between 2.0% and 3.5%. Another preferred range of benzoyl peroxide concentrations is between 3.5% and 4.0%. A most preferred concentration of benzoyl peroxide is about 2.5%, that is between 2.3% and 2.7%. Another most preferred concentration of benzoyl peroxide is about 3.75%, that is between 3.6% and 3.9%.

The formulation may be one of many topical formulation types containing water as the major ingredient, including solutions, gels, creams, sprays and foams. It is preferred, although not required, that the formulation be in the form of an aqueous gel. Accordingly, the formulation of the invention may contain a gelling or thickening agent. Any gelling agent that is water-dispersible, is suitable for use on epithelial tissue such as skin, and forms an aqueous gel of substantially uniform consistency, is suitable for use in the composition of the invention. One preferred gelling agent is hydroxypropylcellulose, such as that sold under the tradename KLUCEL® (Hercules Incorporated, Wilmington, Del., USA). Another preferred gelling agent is hydroxyethylcellulose, such as that sold under the tradename NATROSOL® (Hercules Incorporated). Other suitable gelling agents include carboxyvinyl polymers, also known as carbomers, such as are sold under the tradename CARBOPOL® 934, 940, 941, 980, and 981 (B.F. Goodrich Co., Akron, Ohio, USA), ETD 2020™, and ULTREZ® (Noveon, Inc., Cleveland, Ohio, USA). Additional suitable gelling agents are polyvinyl alcohol, polyethylene oxides, propylene glycol alginates, methylcellulose, hydroxypropylmethylcellulose and natural polymeric gums such as xanthan, and carrageenan. The concentration of gelling agent in the composition may be varied depending on several factors, including the desired degree of stabilization of the BPO suspension and desired viscosity of the gel composition.

If desired, the formulation of the invention may further include additional pharmaceutically acceptable excipients typically used in formulations and known to those skilled in the art. Such excipients include, for example, humectants, emollients, pH stabilizing agents, preservatives, chelating agents, and anti-oxidants.

The formulation of the invention can be used to treat acne by applying the formulation to affected areas of the skin, such as on the face, neck, back, and chest. The formulation is preferably applied one or more times daily for a time sufficient to ameliorate the signs of acne. It has been surprisingly discovered that formulations of the invention containing 2.5% benzoyl peroxide or 3.75% benzoyl peroxide have efficacy in treating acne that is comparable to that obtained with formulations containing 5.0% benzoyl peroxide, the preparations also containing an antibiotic, clindamycin 1%. It is further surprising that this comparable efficacy was observed when the formulations of the invention were applied only once daily and the formulations containing 5.0% benzoyl peroxide were applied twice daily. Unexpectedly, a formulation containing 3.75% benzoyl peroxide was found to exhibit efficacy comparable to, or better than, that of a formulation containing 5% benzoyl peroxide in treating acne while maintaining an adverse event profile comparable to a formulation containing 2.5% benzoyl peroxide.

The formulation of the invention may also be used in the treatment of acne rosacea. In treating acne rosacea, the formulation of the invention is applied to affected areas, preferably one or more times daily for a time sufficient to ameliorate the signs and symptoms of acne rosacea.

The formulation of the invention may be made by any means by which the components of the invention are combined to provide a pharmaceutical formulation. For example, a suspension of benzoyl peroxide may be made by combining water, the water-miscible organic solvent, and benzoyl peroxide. Preferably, the combination is mixed, such as by stirring, sonicating, milling, and/or shaking, to produce a uniform suspension of benzoyl peroxide particles in the water and organic solvent. Additional ingredients, such as a gelling agent and other excipients, may be added either before or after the uniform suspension is obtained.

If an additional anti-acne medication is included in the formulation, it may be combined with the other components prior to or after forming the suspension of benzoyl peroxide. An alternative is to provide a separate aqueous solution of the anti-acne medication, such as clindamycin, and combine this solution with the benzoyl peroxide suspension to obtain a final formulation.

The invention is further illustrated in the following examples which are meant to be exemplary and not limiting.

Example 1—Exemplary Formulation of the Invention

A pharmaceutical formulation of the invention was made containing the following components as shown in Table 1.

TABLE 1

| COMPONENT | % w/w |
|---|---|
| Benzoyl peroxide | 2.5 |
| Propylene glycol | 5.0 |
| Carbopol 980 ® | 1.75 |
| Potassium hydroxide | 0.5 |
| Water | QS 100 (90.25) |

Example 2—Additional Exemplary Formulations of the Invention

Two pharmaceutical formulations of the invention containing an anti-acne medication in addition to benzoyl peroxide was made containing the following components as shown in Table 2.

TABLE 2

| COMPONENT | Formulation A (% w/w) | Formulation AA (% w/w) |
|---|---|---|
| Benzoyl peroxide | 2.5 | 3.75 |
| Propylene glycol | 5.0 | 5.0 |
| Clindamycin phosphate | 1.2* | 1.2 |
| Carbopol 980 ® | 1.75 | 1.75 |
| Potassium hydroxide | 0.5 | 0.5 |
| Water | QS 100 (89.05) | QS 100 (87.8) |

*equivalent to 1.0% clindamycin

Example 3—Comparative Efficacy

The aqueous gel formulation of Example 2 containing 2.5% benzoyl peroxide, 5% propylene glycol, 89% water, and 1% clindamycin was tested for efficacy in the treatment of acne lesions in a large clinical study in which 399 patients were treated. This formulation of the invention is Formulation A. A similar aqueous gel formulation containing 5.0% benzoyl peroxide, 10% propylene glycol, 82.5% water, and 1.0% clindamycin was made and tested for efficacy in the treatment of acne lesions in a second clinical study of very similar design. This formulation, which is not of the invention, is Formulation B. These results were compared with data provided in the prescribing information on the efficacy of an aqueous gel commercial product containing 5.0% benzoyl peroxide, 1% clindamycin, dioctyl sodium sulfosuccinate (surfactant), and water (BenzaClin® Topical Gel, Dermik Laboratories, Bridgewater, N.J.). This prior art formulation is Formulation C. Formulations A and B contained no surfactant. Formulation A was applied only once daily whereas Formulations B and C, each of which contain 5.0% benzoyl peroxide, were applied twice daily during the 12 week treatment period. Formulation A was tested after 12 weeks of application. The data for Formulations B and C is following 10 weeks of application. A formulation containing 3.75% benzoyl peroxide, Formulation AA, was also tested according to the procedure for Formulation A. Formulation AA also contained propylene glycol (5.0% w/w), clindamycin phosphate (1.2% w/w), Carbopol 980® (1.75% w/w), potassium hydroxide (0.5% w/w), and water (QS 100%). Formulation AA contained no surfactant.

Test subjects were instructed to apply the formulation to the face, either twice daily for Formulations B and C or once daily for Formulations A and AA. After 10 weeks for Formulations B and C, and after 12 weeks for Formulations A and AA, the mean percent reduction in inflammatory lesions and non-inflammatory acne lesions was determined. The percentage reduction in inflammatory lesions (pustules and papules) was calculated by subtracting the total inflammatory lesion counts at the end of the study (10 or 12 weeks) from the baseline total inflammatory lesion counts, times 100, and divided by the baseline total inflammatory lesion counts. Non-inflammatory lesions comprised open comedones and closed comedones, and the percentage reduction in non-inflammatory lesions was calculated in the same way. The results of this acne study are shown in Table 3.

TABLE 3

|  | Formulation A | Formulation B | Formulation C | Formulation AA |
|---|---|---|---|---|
| Number of Subjects | 399 | 481 | 215 | 253 |
| Mean % Reduction in Inflammatory Acne Lesions | 48.8 | 59.2 | 53.5 | 60.6 |
| Mean % Reduction in Non-inflammatory Acne Lesions | 42.6 | 51.0 | 36.1 | 51.6 |

The data of Table 3 shows that the efficacy of Formulation A containing only 2.5% benzoyl peroxide was similar to that of Formulations B and C. These results are especially surprising in view of the fact that Formulation A was applied only once daily whereas Formulations B and C were applied twice daily. Formulation AA containing 3.75% benzoyl peroxide and 1.2% clindamycin phosphate exhibited higher efficacy than the Formulation A containing 2.5% benzoyl peroxide and 1.2% clindamycin phosphate. Surprisingly, Formulation AA also exhibited higher efficacy than Formulations B and C containing 5% benzoyl peroxide.

Example 4—Irritation Potential

Formulations A and B of Example 3, each containing benzoyl peroxide and 1.0% clindamycin, were tested to determine the comparative irritation potential of these two formulations. Formulation A of the invention contains 2.5% benzoyl peroxide, propylene glycol at two times the concentration of the benzoyl peroxide, and water at a concentration 17.8 times that of the propylene glycol. Formulation B contains 5.0% benzoyl peroxide, propylene glycol at two times the concentration of the benzoyl peroxide, and water at a concentration 8.25 times that of the propylene glycol.

Gel formulations A and B were applied under separate occlusive patches to the backs of 33 healthy subjects three times a week for three weeks. Each application was observed 48 hours following each application for signs of irritation or inflammation by evaluators and assigned a score using a standardized grading system for irritation on a severity scale of 0 (no sign of irritation) to 4 (erythema with edema and blistering). Data from this study shows that use of Formulation A of the invention produced a 33% decrease in overall cumulative irritation score compared to use of Formulation B.

In addition, Formula A and Formulation AA exhibited similar adverse event profiles. The expectation was that the number of subjects reporting adverse events (for example, redness, itching, and burning) would be higher for Formulation AA, having a higher concentration of benzoyl peroxide, than for Formulation A. The unexpected results of combination AA are shown in Table 4. The number of subjects reporting one or more adverse events were similar for Formulation A and Formulation AA, and both formulations were similar to vehicle.

TABLE 4

|  | Formulation AA | Vehicle AA | Formulation A | Vehicle A |
|---|---|---|---|---|
| Number of Subjects | 243 | 236 | 386 | 188 |
| Number of subjects who reported one or more adverse events | 54 of 243 (22.2%) | 57 of 236 (24.2) | 106 of 386 (27.5) | 50 of 188 (26.6) |
| Number of adverse events related to or possibly related to study medication[a] | 4 of 68 (5.8%) | 7 of 71 (9.9%) | 5 of 139 (3.6%) | 4 of 78 (5.1%) |

[a]Based on total number of events.

Further modifications, uses, and applications of the invention described herein will be apparent to those skilled in the art. It is intended that such modifications be encompassed in the above description and in the following claims.

What is claimed is:

1. A method for treating acne rosacea, comprising applying to the skin of a patient in need thereof an aqueous suspension formulation comprising 2.5% w/w to 4.5% w/w benzoyl peroxide, about 1.2% w/w clindamycin phosphate, propylene glycol, a gelling agent, and water;
   wherein the combined concentration of water and propylene glycol is sufficient to provide a suspension of benzoyl peroxide in a saturated solution of benzoyl peroxide,
   wherein the ratio of water to propylene glycol in the formulation ranges from 12:1 to 20:1,
   wherein the concentration of the propylene glycol is one to four times the concentration of the benzoyl peroxide, and
   wherein the formulation is applied once a day for up to 12 weeks to the skin of the patient.

2. The method of claim 1, wherein the concentration of benzoyl peroxide in the formulation ranges from 2.5% to 3.5% w/w.

3. The method of claim 1, wherein the concentration of benzoyl peroxide in the formulation is about 3.5% w/w.

4. The method of claim 1, wherein the concentration of propylene glycol in the formulation is about 5.0% w/w and the ratio of water to propylene glycol in the formulation ranges from 12:1 to 18:1.

5. The method of claim 1, wherein the gelling agent is selected from the group consisting of hydroxypropylcellulose, hydroxyethylcellulose, a carboxyvinyl polymer, polyvinyl alcohol, a polyethylene oxide, a propylene glycol alginate, methylcellulose, hydroxypropylmethylcellulose, xanthan gum, and carrageenan.

6. The method of claim 5, wherein the gelling agent is a carboxyvinyl polymer.

7. The method of claim 1, wherein the formulation is free of surfactant.

8. The method of claim 1, wherein the formulation contains a surfactant.

\* \* \* \* \*